United States Patent [19]
Weeden et al.

[11] Patent Number: 6,063,616
[45] Date of Patent: May 16, 2000

[54] MATRIX MILL FOR DNA EXTRACTION

[75] Inventors: Norman F. Weeden, Geneva; Dale Loomis, Freeville; Joseph A. Celeste, Watkins Glen, all of N.Y.

[73] Assignee: Cornell Research Foundation, Inc., Ithaca, N.Y.

[21] Appl. No.: 08/963,746

[22] Filed: Nov. 4, 1997

Related U.S. Application Data

[60] Provisional application No. 60/029,934, Nov. 4, 1996.

[51] Int. Cl.$^7$ ............................. C12M 3/08; B01D 35/06; G01N 1/00
[52] U.S. Cl. .................................. 435/283.1; 435/306.1; 435/803; 210/695; 210/222; 436/174; 436/177; 422/186; 422/186.01
[58] Field of Search ............................. 435/803, 6, 91.2, 435/173.4, 173.7, 173.9, 306.1, 288.4, 283.1; 935/1, 19; 210/695, 222; 436/31, 17 A, 177; 422/186, 186.01

[56] References Cited

U.S. PATENT DOCUMENTS

| | | | |
|---|---|---|---|
| 2,458,692 | 1/1949 | Downer | 259/92 |
| 2,735,232 | 2/1956 | Simjian | 51/7 |
| 3,219,318 | 11/1965 | Hershler | 259/1 |
| 3,848,363 | 11/1974 | Lovness et al. | 51/7 |
| 4,134,553 | 1/1979 | Steinort et al. | 241/34 |
| 4,134,557 | 1/1979 | Kazzaru et al. | 241/170 |
| 4,632,316 | 12/1986 | Watanabe et al. | 241/26 |
| 4,911,806 | 3/1990 | Hofmann | 204/180.1 |
| 4,988,618 | 1/1991 | Li et al. | 435/6 |
| 5,074,474 | 12/1991 | Golz et al. | 241/1 |
| 5,464,773 | 11/1995 | Melendez et al. | 435/306.1 |
| 5,508,164 | 4/1996 | Kausch et al. | 435/6 |
| 5,512,439 | 4/1996 | Hornes et al. | 435/6 |
| 5,567,326 | 10/1996 | Ekenberg et al. | 210/296 |

OTHER PUBLICATIONS

Gu, W.K., et al, Large–scale, cost–effective screening of PCR products in marker–assisted selection application, 1995, Theor. Applied Genet. 91:465–470.

Saiki, R.K., et al, 1988, Primer–directed enzymatic amplification of DNA with a thermostable DNA polymerase, Science 239:487–491.

Wang, H., et al., 1993, A sample method of preparing plant samples of PCR, Nucleic Acids Res., 21:4153–4154.

Foster, A., 1992, Cell disruption: Breaking up is hard to do, Biotech, vol. 10:1539–41.

*Primary Examiner*—Keith D. MacMillan
*Assistant Examiner*—P Ponnalun
*Attorney, Agent, or Firm*—Brown, Pinnisi & Michaels, P.C.

[57] ABSTRACT

The device and methods herein disclosed were developed to allow a large number of small samples of organic tissue to be processed. The goal was to allow for the capture of these intracellular contents for study, use, and/or amplification. Though the device and specific protocols can be used to retrieve a variety of intracellular molecules one of the preferred embodiments particularly lends itself to the extraction of DNA. The electromagnetic device uses a set of terraced coils controlled in such a matter as to continually alternate polarity and thereby emulate the random motion of a manual mortal and pestle. This simulation of random motion is created through the arrangement of coils found in this invention. Methods were also developed to aid in the retrieval of DNA or other intracellular components using this device such that these components can be isolated and then used for study, amplification, or a variety of different purposes. Essentially the enclosed invention discloses a device and methodology which will allow for the rapid processing of many small tissue samples. This will assist in making such procedures as genotyping, genetic analysis, and gene mapping faster and more reliable on a large scale.

17 Claims, 8 Drawing Sheets

MATRIX MILL FOR DNA EXTRACTION

REFERENCE TO PROVISIONAL APPLICATION

This application claims an invention which was disclosed in Provisional Application No. 60/029,934, filed Nov. 4, 1996, entitled "Matrix Mill For DNA Extraction". The benefit under 35 USC §119(e) of the United States provisional application is hereby claimed, and the aforementioned application is hereby incorporated herein by reference.

FIELD OF THE INVENTION

The invention relates to a electromagnetic device, and the development of methods that enhance the ability to accumulate and use intracellular components. More particularly, the invention pertains to the use of electromagnetism for the extraction of DNA sequences, and for rapidly genotyping large sets of these samples.

BACKGROUND OF THE INVENTION

Biotechnology is a rapidly advancing field which requires the development of new and novel devices, and techniques to keep pace with the rest of the advances in a given field. These developments generally aid scientific investigators in the ability to isolate and investigate the constituents of various cellular forms. Analysis on this level is most often done through the investigation of an organism's, or cell type's, deoxyribonucleic acid (DNA). To better understand the genetic makeup of a given organism its DNA must be made available for the physical interactions with different chemicals, probes, and/or enzymes which are necessary with today's science. The process of making DNA available for study, as demonstrated in prior art can be problematic in those instances where the method is disruptive to the DNA. This is especially true where the cells/tissue are difficult to lyse without destroying the DNA molecules.

The methods used to liberate intracellular DNA are many and include, chemical systems designed to destroy the cell membrane, and cell wall if present, sonic wave systems, mechanical systems which essentially rip the cell open allowing the internal contents to be accessible, and physical pressure systems wherein the cells are pressured open. The balance then between efficiently lysing a cell and avoiding DNA degradation is a difficult one. Moreover, the processes, as they exist today, are often too expensive, and take to much effort to be completed successfully on a large scale. The alkaline solution treatment for extraction represented a significant improvement in DNA extraction technology, making such extraction easier, however it needed to be automated to cope with the demands of the research laboratories and corporations for powerful methods of genotyping large samples.

Therefore, there is a need for a simple method for extracting DNA from tissue samples on a large scale. The method and device disclosed herein attempts to solve this problem and were originally developed to aid in the rapid genotyping of large numbers of organisms. The use of oligonucleotide primers, typically 24-mers, for the development of genetic markers, and genotyping generally, has significantly increased the speed and ease by which DNA fragments tightly linked to the genes of interest can be isolated and identified. One problem encountered, however, is the expense of performing such tests. The expenses include not only material and supplies, but also the less definable costs such a quality of technical personnel, laboratory space, etc. This is especially true for those individuals and corporations involved in the seed or animal stock quality control applications.

SUMMARY OF THE INVENTION

The objective of this invention is to provide a device, and a method of using that device which will allow the rapid genotyping of DNA samples as well as the collection and manipulation of other intracellular components as desired. DNA samples are collected after the organic material in question is subjected to maceration in one of a plurality of wells. The DNA produced therefrom can be amplified through PCR or RFLP procedures. Other components of the freed cytosol should also be of use in scientific investigation and/or commercial development or research.

The invention disclosed herein includes a method for the lysing of cells and the retrieval of their DNA which includes: enclosing the cellular material in a tube or similar container, along with a material capable of disrupting the sample material releasing the intracellular contents, and a micropestle of ferrous material capable of the maceration of the sample when subjected to pulses of electromagnetic energy; subjecting the container to said maceration through the operation of the device herein disclosed. This process further comprises the step of collecting the desired cellular components, specifically DNA, from the released intracellular cytosol. The recovery system can be varied according to cell or tissue type, which would essentially include the use of slightly different buffering systems. Also variable is the use of enzymes or other compounds present in the buffering system which will maximize the integrity and preservation of the target molecule or compound. In this vein, an anti-DNAse enzyme would be present in the buffering system to prevent anti-DNA endonucleases or other enzymes from damaging and/or cleaving the DNA liberated from the sample. Similar precautions would be taken if the desired target were an RNA species (e.g. anti-RNAse's in the buffer), or other molecule. For the recovery of specific molecules such as rRNA, specified protocols are used.

Through the use of this device a huge number of biological material can be prepared for genotyping or investigation into intracellular components. This includes such different organisms from plants to bacteria to mammals, to mycoplasmas and other more exotic organic structures— essentially any organic structure that contains DNA.

One protocol involves the maceration of cells in a alkaline environment, through which DNA or other intracellular components are extracted. The method developed by this application includes the use of an electromagnetic device designed to facilitate the large scale availability of intracellular components for study, in a short period. This device and method optimize the retrieval of DNA, or other specific intracellular components while allowing an efficient and large scale processing of samples. The specific target is the cellular DNA which is extracted through use of chemical means, specifically an alkaline environment in the presence of a buffering system in combination with the of the electromagnetic device herein disclosed. The samples are place in a plurality of non-ferrous tubes, 96 in the preferred embodiment, which then have a pin or "micro pestle," with at least a ferrous core inserted into the tubes. This micropestle, typically of stainless steel but if fully coated the core could be of any ferrous material, is coated with a non-reactive material, usually Teflon but could be a non-reactive plastic-type coating. The use of electromagnetism to provide the energy for the movement of these pins or pestles allows the device to approximate the random movement of the manual method of mortar-and-pestle preparation typically used for DNA extractions.

The matrix mill is designed to simultaneously pulverize or macerate small samples of animal or plant tissue for the purpose of extracting DNA or other nucleic acid. The need for such a machine has arisen recently as a result of two developments in DNA technology. The first development was the use of the polymerase chain reaction (PCR) to specifically amplify fragments of DNA (Saiki et al., 1988) using a very small amount of the initial 'template' DNA. The second development was the demonstration that DNA could be isolated from plant samples by extraction in 0.1M sodium hydroxide (Wang et al., 1993). Gu et al. (1995) took advantage of these two advances to develop a technique for screening large numbers of DNA samples. However, for most efficient use of the technique, a machine was still required that could quickly and easily extract DNA from a large number of samples. Automated DNA extraction machines have been developed before (e.g. at DuPont), but these have been large, expensive devices based on more complex DNA extraction procedures and are not appropriate for the typical molecular biology laboratory or, more importantly, small laboratories associated with small research corporations or institutes, breeding programs, or hospitals, where large scale DNA screening is currently desirable but often not practical, due to cost or technical limitations.

The device used herein is composed of a base with wells for individual samples, the wells or microtiter tubes composed of a non-magnetic material. Into each well is inserted a pestle composed of a ferrous material, coated or uncoated, which may, but need not generate its own magnetic field.

DETAILED DESCRIPTION

The matrix mill performs DNA extraction simply and inexpensively. The design uses electromagnetism in a novel application. Basically, a pulsating electromagnetic field drives 96 separate "motors" (in a 12×8 cell matrix), each with approximately the same force, so that up to 96 samples can be macerated and prepared simultaneously.

Figure 1:
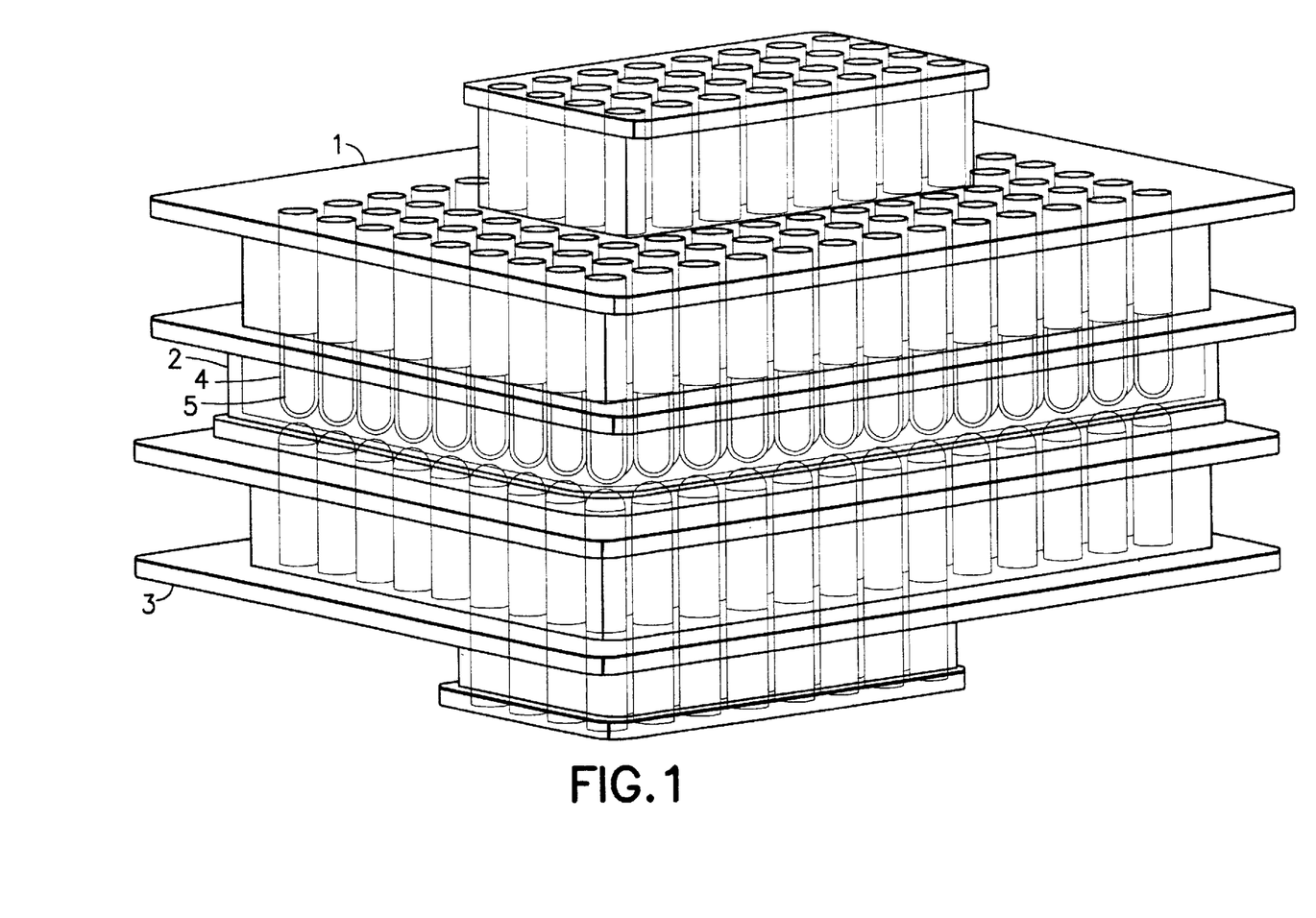
FIG. 1 shows an overall assembled view of the invention.
Figure 2:
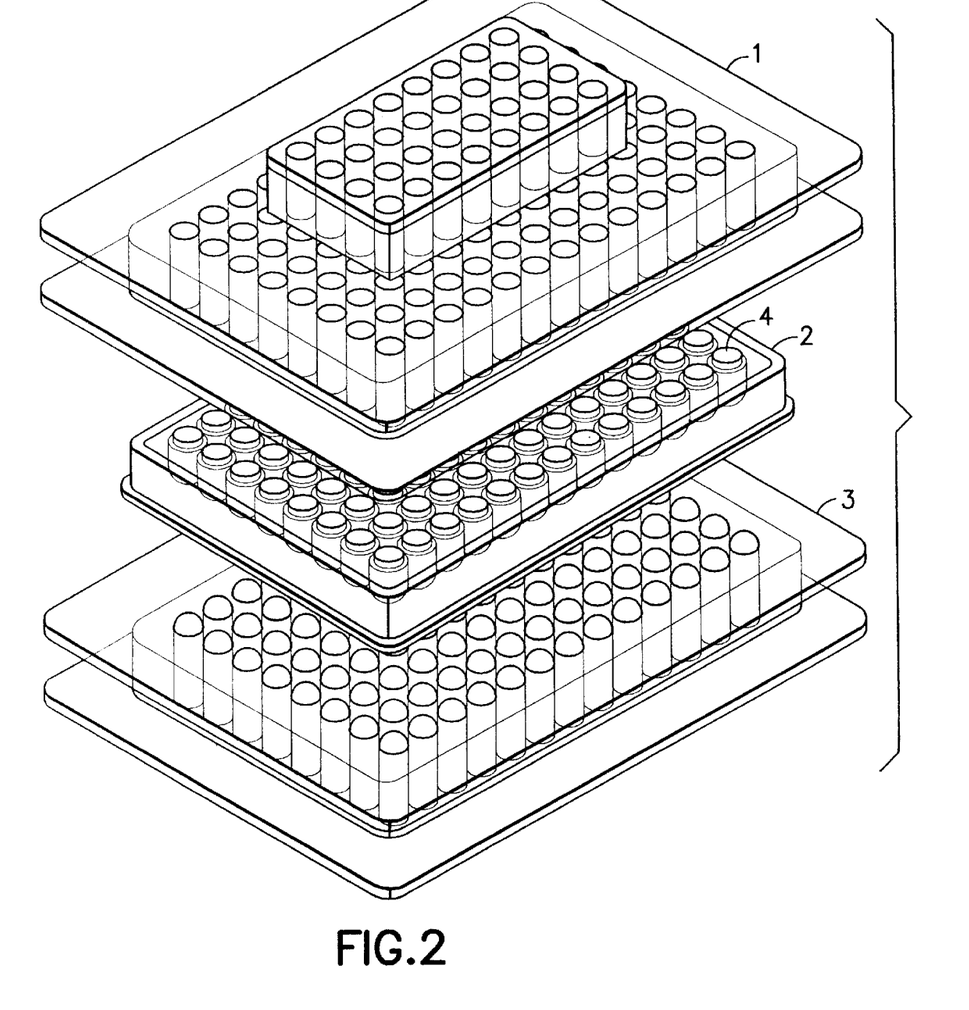
FIG. 2 shows an exploded view of the invention.

FIG. 1 shows the matrix mill of the invention, in assembled status, and FIG. 2 shows the matrix mill with the basic components separated. The basic components of the matrix mill are:

the upper (1) and lower (3) electromagnetic driver frame assemblies, which together form a means for generating the varying electromagnetic field used in the invention;

a microtiter tray (2) or other sample holder arrangement, comprising a plurality of nonmagnetic sample containers such as wells (4) or individual microtubes arranged in a matrix;

a magnetic micropestle (5) in each sample container.

Figure 3:
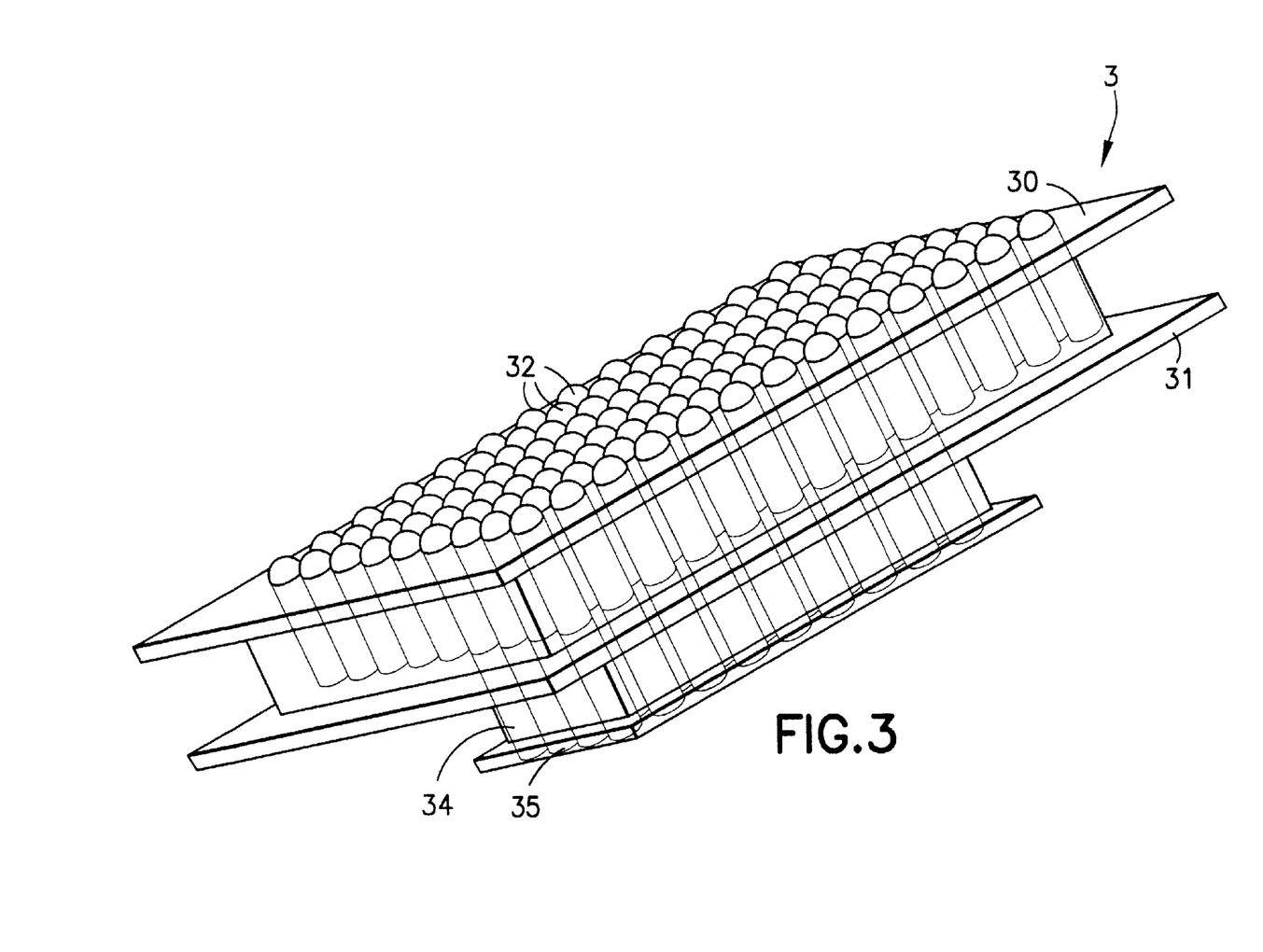
FIG. 3 shows a view of the lower frame assembly of the invention.
Figure 4:
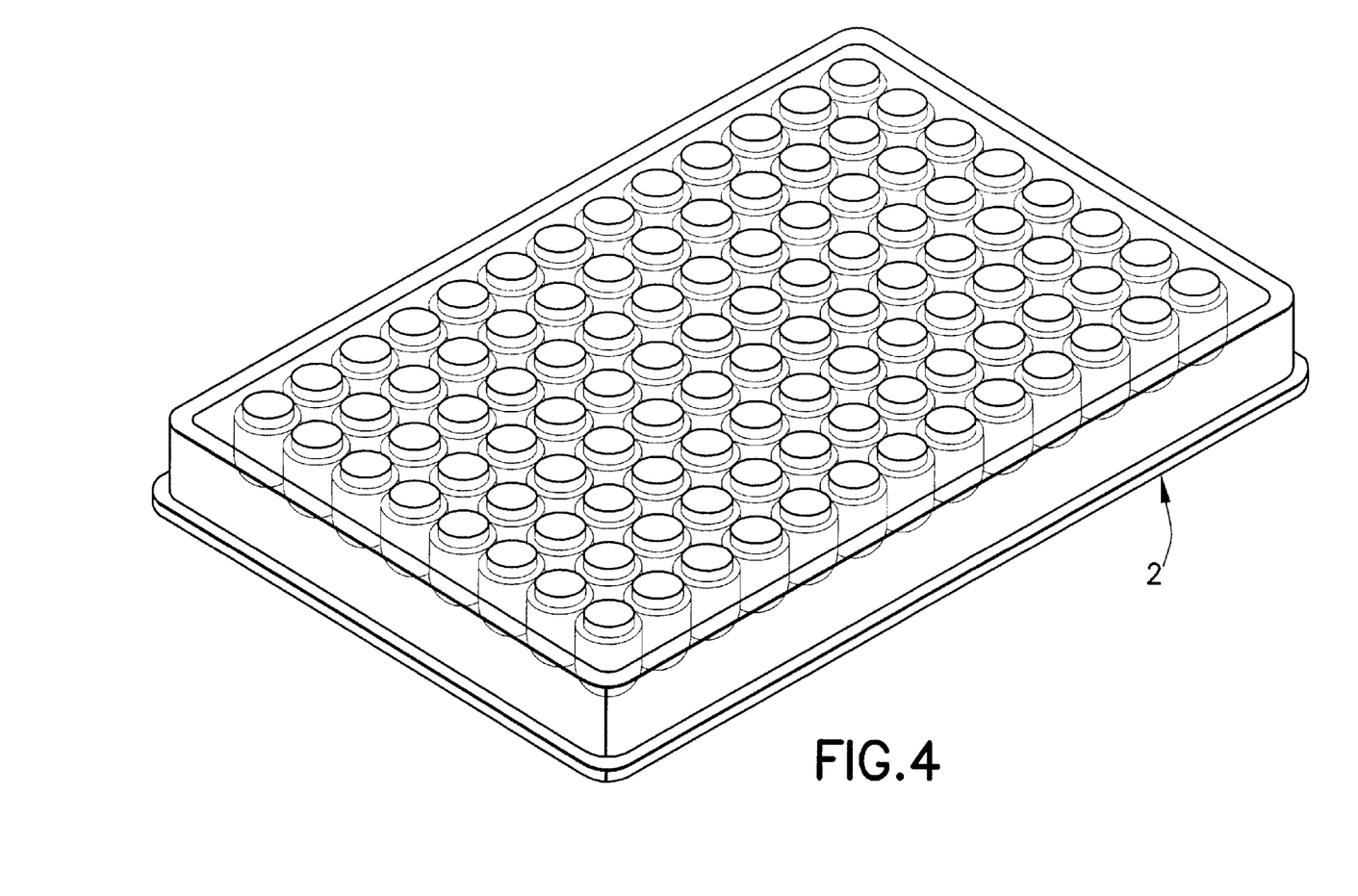
FIG. 4 shows a view of the microtiter assay tray used in the invention.
Figure 5:
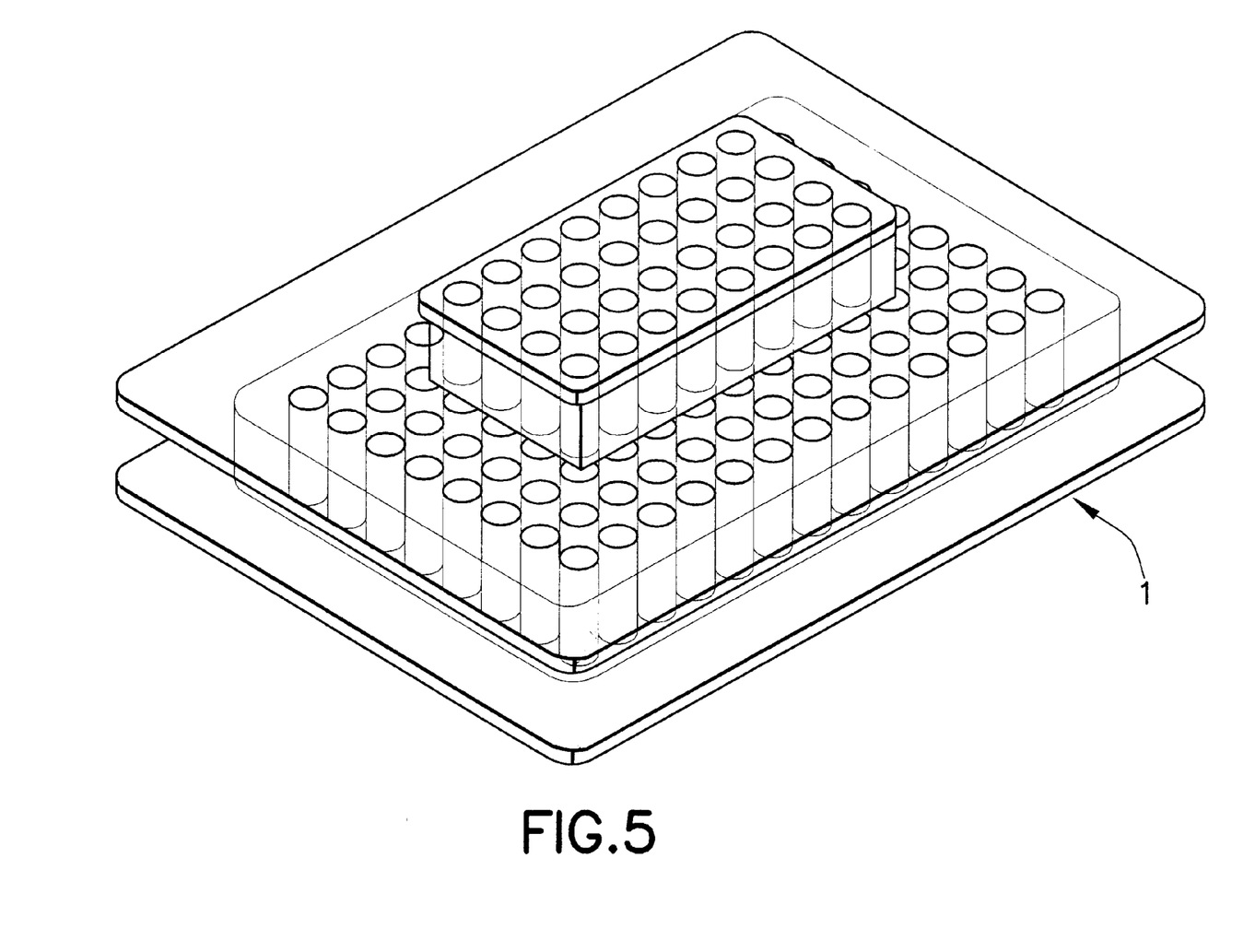
FIG. 5 shows a view of the upper frame assembly of the invention.

FIGS. 3 and 5 show the lower and upper driver frame assemblies, respectively. As the two assemblies are symmetrical, the following discussion will be directed to FIG. 3, but it will be understood that the upper frame shown in FIG. 5 is identical.

The electromagnetic driver frame assembly (3) comprises a plurality of driver cores (32), one for each sample holder in the matrix, supported and oriented by an appropriately designed frame structure. In a preferred embodiment, the driver cores (32) are supported by plates (30), (31) and (35). The driver cores (32) are surrounded by electromagnetic coils (omitted in this drawing to show the core structure). In order to maintain a uniform magnetic field strength across the matrix, the central driver cores (34) are longer than those cores (33) around the periphery of the frame assembly, allowing a second set of coils to be added.

Figure 6:
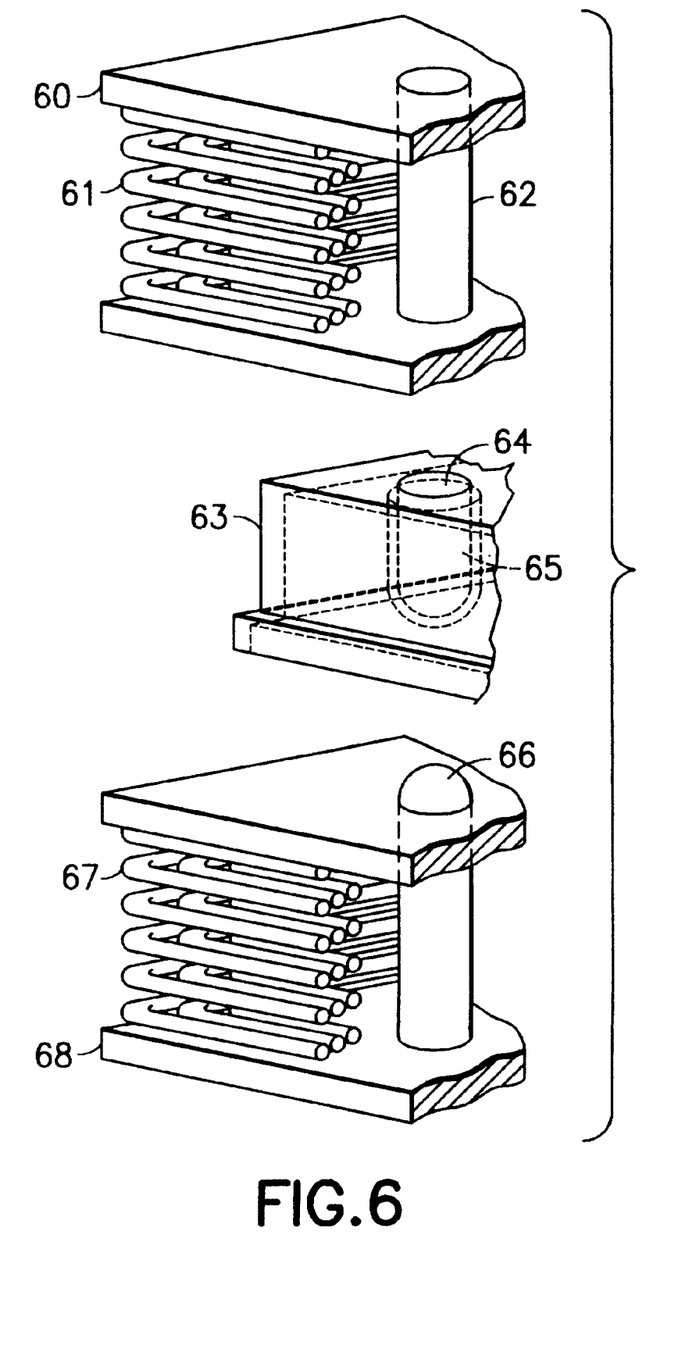
FIG. 6 shows an exploded detail view of a single matrix element of the invention.

A discussion of a single element of the matrix, as shown in FIG. 6, provides the clearest initial description of the grinding process. Well (64), part of a larger assay plate (63) and containing a target sample, is placed into the matrix mill (1) with at least a magnetic core (62, 66) in proximity thereto. Thereafter grinding rod (65) is inserted into the well (64) through the use of an appropriately designed frame structure (60). After insertion of the grinding rod (65) the sample is ready to be processed when the field generating coil assembly (61) is energized. Once energized, the upper (61) and lower (67) assemblies, driven by the alternating current provided by the power source through the coils (61) located in proximity to the cores (62, 66) cause the magnetically active grinder rod (65) to begin the maceration of the sample material within the well.

It should be noted that for the purposes of this application the term "matrix" means a plurality of elements attached to one another in a one or two dimensional array, into which samples of organic material can be placed for processing. This matrix consists of one or more rows of well elements, preferably a standard 96-well laboratory plate (8×12 or 96 individual wells).

In the device described herein there are two electromagnetic poles opposing a sample container holding a sample to be crushed. The sample container also holds a small stainless steel (ferro-magnetic) grinding pestle. Opposing magnetic fields alternately pulse and drive the grinding rod or pestle in a vertical motion to pulverize the sample. Although this basic description appears simple, there are a number of technical issues which were resolved. To create upward pulsing/vibrating to encourage the movement of the sample under the grinding pestle, a pulsed positive sinusoidal wave front was used, through the device. This wave form alternates its polarity every primary cycle to reduce residual polarized magnetism from developing in the grinding pestle. The polarity switch controls and inverts the polarity in each half of the device every 400 milliseconds. This alternation of polarity keeps the pin/pestle from becoming permanently magnetized in one polar direction. Magnetized pins seriously reduce the effectiveness of the machine.

The prior art had difficulty insuring the random motion of the ferrous pins/pestles used to macerate the samples. It was known that a minimal magnetic field is required to set the pins/pestles in motion, but is this amount of force was also known to be insufficient to maintain this random motion in a stable manner. Thus, in order to maintain the random motion of the micro-pestles in a stable condition the magnetic field was raised. This increase in intensity of the field caused another problem, the increased magnetic field gradually reduced the "randomness" of movement for the pins/pestles, and was detrimental to the overall maceration and eventual DNA extraction, due to the single polar orientation discussed above. This reduction of randomness is caused by frictional forces, magnetic sucking force, repulsive forces, and collision.

Thus, a significant design problem was to emulate the manual, and random, method of mortar-and-pestle preparation typically used for nucleic acid extraction's (e.g. DNA), while avoiding the problems just discussed. A wide range of motions (vertical, horizontal, sliding, smashing, etc.) are involved in this type of mortar and pestle extraction. Such motions were successfully mimicked by developing a complex driver system that relies on variable time, event, force, and direction movements on selected pins/pestles of ferrous material.

A magnetically active core is needed if the outer surface of said core is to be coated with Teflon or other durable non-reactive substance. If the pestle is uncoated, or only partially coated, then 416 Stainless Steel is used for its corrosion resistance properties if only a portion is uncoated.

The field driver is defined below in outline form with aid of the attached illustration. The power source for the driver was a low voltage alternating current:

60 cycle ½ wave (50% duty cycle) sinusoidal current

The upper coil assembly uses the positive ½ wave

Figure 9:
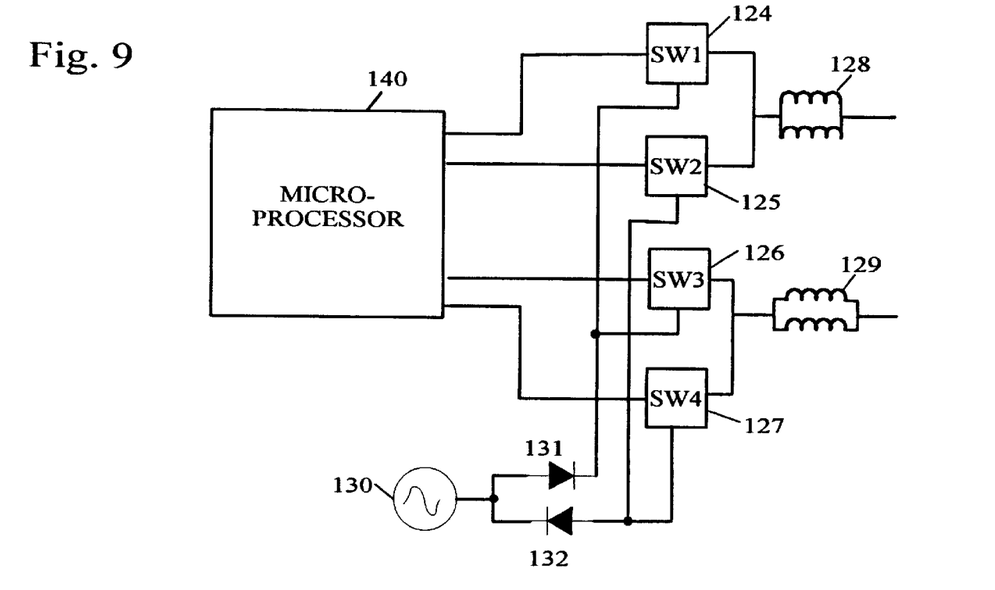
FIG. 9 shows a block diagram of the electromagnet drive circuitry of the invention, in a microprocessor-controlled embodiment.

The lower coil assembly uses the negative ½ wave (see FIG. 9 for graphic description)

Each coil assembly (upper and lower) operates for 200 milliseconds in an alternating fashion, the overall polarity switch operating every 400 milliseconds. When a coil is allowed to operate (200 milliseconds) it is served a 5 millisecond repeating signal, consisting of 2 milliseconds active and 3 milliseconds inactive, helping to maintain the random movement so important to the overall concept. During the active phase voltage may or may not be available to actually drive the coil, based on the relative timing of the 5 millisecond driver period and the timing of the input power wave form, which is operating at a 16 millisecond period with an 8 millisecond power on time. During the power on time the voltage is not constant; rather it is dependent on the input sinusoidal power wave form, as seen in an attached diagram. Thus, each time the 2 millisecond active pulse occurs when input voltage is present, the pulse transferred to the pestle will be of a different magnitude. In summary, the grinding pin/pestle receives a wide variety of different pulse intensities about 20 times every 200, milliseconds, which is 50% of the polarity switch, and is the duration of each coil's driving time.

Combining 96 of these cells, as for a typical 96-well laboratory plate, into a matrix the size and shape of a microliter plate required overcoming additional obstacles. All 96 grinding pestles need to experience approximately the same changes in the strength of the field so that all samples will be macerated approximately evenly. In normal applications an electromagnet develops a strong magnetic field at its center, with diminishing force as one moves away from the axis of the field core. Through empirical experimentation we found that an electromagnetic coil structure, when "loaded" with discreet ferro-magnetic pins/pestles, exhibits the opposite effect (e.g. field strength diminished toward the center of the matrix). In order to produce a more uniform field throughout the matrix we used a terraced coil structure adding a series of coils and core structures above and below central 24 pestles, as shown in the attached figures, with the inner 24 cores penetrating both coils or each side and coupling together the magnetic fields produced by both coils (e.g. top & bottom). Our solution to this problem worked to evenly distribute the force of the magnetic field on the individual pestles throughout the device.

Operation of machine: The samples of tissue (10 to 100 mg) are placed in separate wells of the microliter plate and 50 microliters of 0.1 M sodium hydroxide are added along with the grinding pestle. The microliter plate is sandwiched between the lower and upper coil structures and the power turned on for between 10 seconds and 5 minutes. At present, we know that 10 seconds of grinding releases sufficient DNA from many plant and other tissues for over 100 PCR assays. We have macerated leaf material for as long as 5 minutes without significant problems. These are optimal grinding conditions for other tissues. Between-sample contamination is prevented by a layer of plastic sheet on the lower surface of the upper coil assembly. The extracts, alkaline in pH, are neutralized with acetic acid or Trizma-HCl (pH 7.0) and diluted for PCR analysis using multi-tipped pipettors. We know of no similar device in any laboratory, either in construction or in the ability to simultaneously process so many samples.

Figure 7:
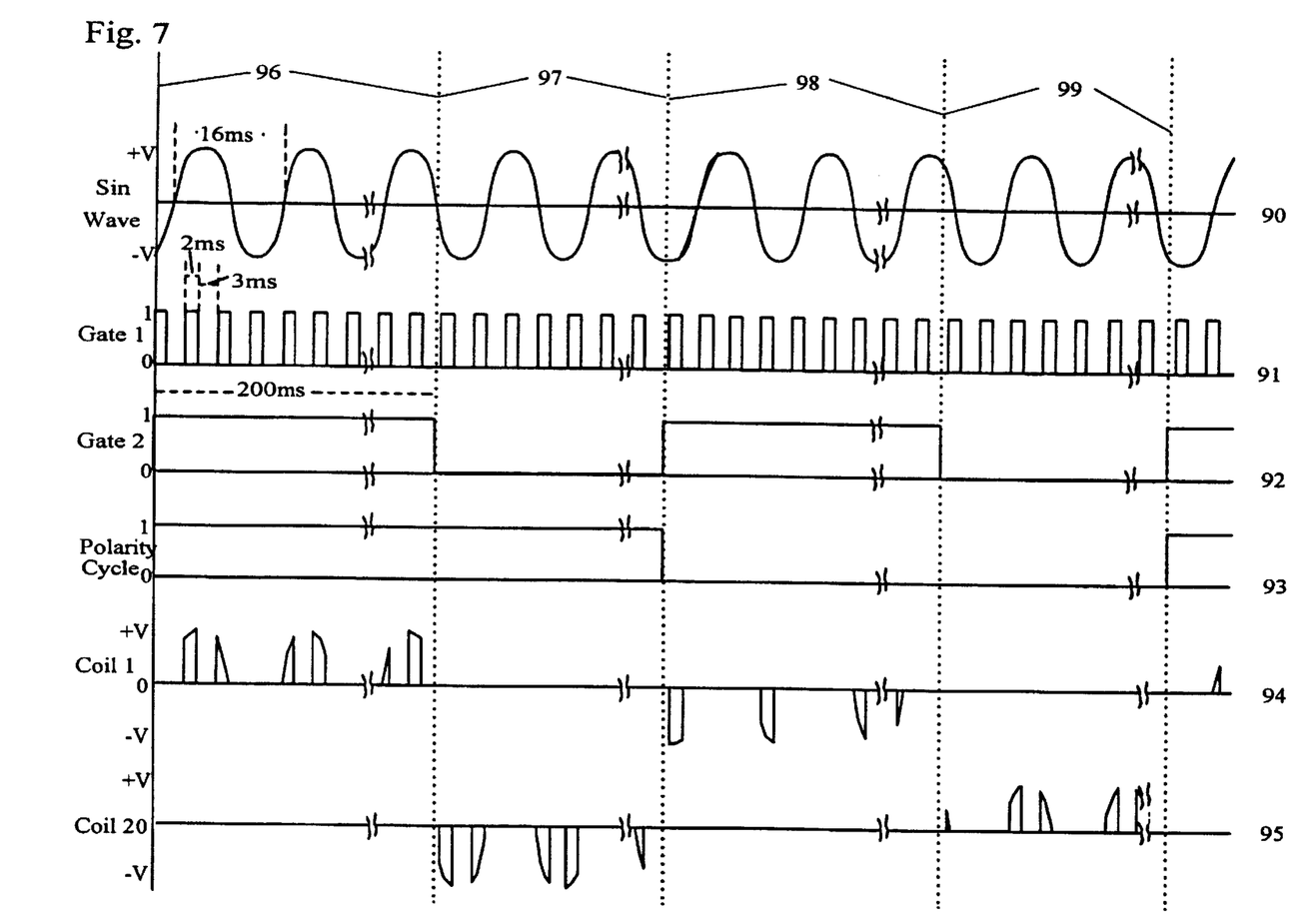
FIG. 7 shows a timing diagram of the signals used to drive the matrix mill of the invention.

FIG. 7 shows a timing diagram of the signals used to drive the coils of the matrix mill. It will be understood that the exact time intervals shown may be varied within the teachings of the invention. For clarity of diagramming, each of the lines is broken, so as to be able to show the 2 ms timing of the gate 1 signal on the same lines as the 400 ms period of the polarity cycle.

The two sets of coils, upper and lower, are driven by Coil 1 (94) and Coil 2 (95) signals, which are pseudo-random in nature as will be seen.

These signals are derived from an AC sine wave (90), which, for convenience, may be derived from the 60 Hz power line by a transformer or the like. The 60 Hz line frequency gives a period of just over 16 ms.

The AC signal (90) is gated by three control signals, Gate 1 (91), Gate 2 (92) and Polarity Cycle (93).

The Gate 1 signal (91) is comprised of 2 ms pulses, separated by 3 ms gaps. The Gate 1 signal (91) is used to "time slice" the AC signal, taking the value of the AC signal during 2 ms slices of the waveform. This 5 ms total timing is unrelated to the 16 ms period of the 60 Hz line signal (90), so that the gated line signal is not repetitive.

Gate 1 (91) is combined with the Gate 2 signal (92), which has a period of 400 ms. During the "on" 200 ms half-cycles (96) and (98), the coil 1 (94) signal is gated "on" and coil 2 (95) is "off". Similarly, during the "off" half-cycles, the coil 2 signal (95) is gated "on", and coil 1 (94) is "off". When the coils are "on", the signal appearing on the coil line is the AC signal (90) "sliced" by gate 1 (91).

The polarity cycle (93) signal has an 800 ms period, synchronized with the gate 2 200 ms signal, which is used to control the polarity of the coil 1 (94) and coil 2 (95) signals. During each 400 ms half-cycle of the polarity cycle, the coil 1 (94) and coil 2 (95) signals are opposite in polarity. The polarity cycle (93) signal causes the polarity of the coil signals to invert for the next cycle of the gate 2 signal, so that, as shown, the pulses sent to coil 1 (94) are positive during half-cycle (96), and negative during half-cycle (98). Similarly, coil 2 (95) is negative during half-cycle (97) and positive during half-cycle (99). The two coils alternate, such that coil 1 is off during gate 2 half-cycles when coil 2 is active, and vice-versa.

Figure 8:
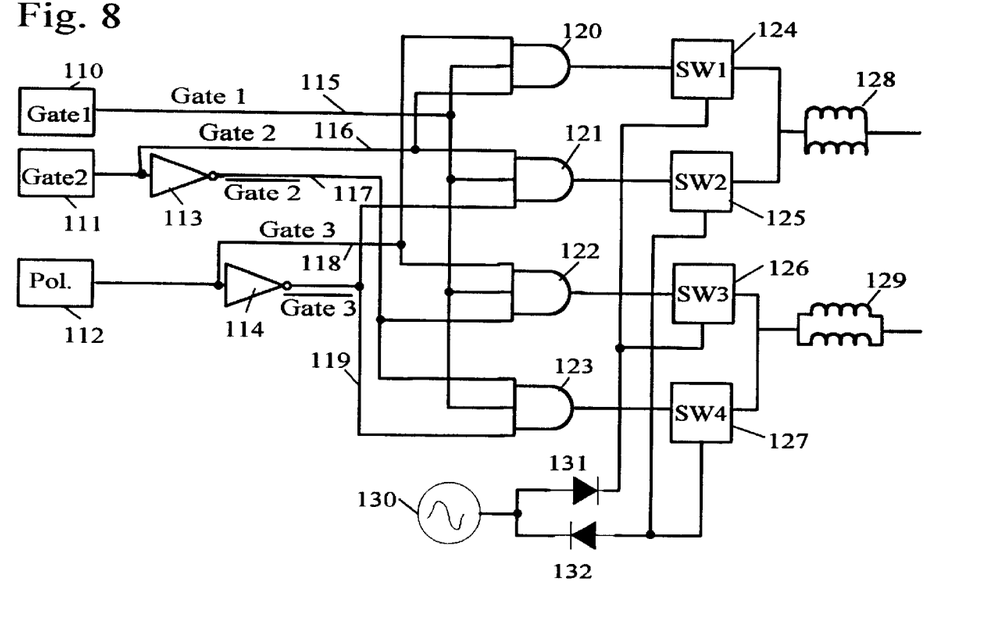
FIG. 8 shows a block diagram of the electromagnet drive circuitry of the invention, in a discrete component embodiment.

FIG. 8 shows a block diagram of the drive electronics for the invention, in an embodiment using discrete components. The upper coils (128) and lower coils (129) are driven by a pair of switches, each: SW1 (124) and SW2 (125) for upper coils (128), SW3 (126) and SW4 (127) for lower coils (129). The switches are driven from the AC source (130) through oppositely polarized diodes (131) and (132). The diodes are connected to the inputs of the switches, such that odd-numbered switches SW1 and SW3 drive the coils with a positive pulse, and even-numbered switches SW2 and SW4 drive the coils with negative-going pulses.

When the switches are activated, the signal on their input is connected to the coils. The switches are activated by drive signals from AND gates (120), (121), (122) and (123), respectively. The inputs to the AND gates are timer pulses generated by timers Gate 1 (110), Gate 2 (111) and Polarity cycle (112), which generate the signals detailed in FIG. 7.

The outputs of gate 2 (111) and pol (112) are fed to inverters (113) and (114), respectively, so that five signals are created: Gate 1 (115), Gate 2 (116), NOT Gate 2 (117), Pol (118) and NOT Pol (119). These signals, connected to the AND gates, control the switches as follows:

Upper coil:
  SW1=Gate 1+Gate 2+Pol
  SW2=Gate 1+Gate 2+NOT Pol
Lower coil:
  SW3=Gate 1+NOT Gate 2+Pol
  SW4=Gate 1+NOT Gate 2+NOT Pol FIG. 9 shows a microprocessor controlled embodiment of the invention, in which a microprocessor (140) is used to produce the signals above, instead of discrete components.

The preferred embodiment of the device includes the provision of random seeming movements for the "micropestle." That is, vibrational movement and/or oscillating movements, provided for in the disclosed device avoid the polarization of the ferrous pin or micro-pestle within the sample well. This is achieved through the use of millise­conds pulses, which can be varied to suit the tissue being macerated, through the electromagnetic device herein described which is itself holding a plurality of samples for testing generating a sinusoidal wave front and "random" motion. The use of electromagnetic pulses to drive the maceration of the sample avoids the problem of dealing with a motorized device, present in much of the prior art, which varies its effective results as the device is heated up through use. The control of the microprocessors integral to the function of the machine can be physical signals (i.e. endgated), but in the current preferred embodiment are controlled through the use of an integrated minicomputer and software tasked to this process.

The machine has been found to give excellent DNA extracts for several tissue types including pea (*Pisum Sativum*), bean (*Phaseolus Vulgaris*), cucumber, pepper, and broccoli. The most convenient method for sampling tissue that we have found is to use a cork borer or similar device that can take circular samples of tissue from 0.8 to 1.5 cm., in diameter, so as to fit in the bottom of the wells wherein the maceration will occur. These samples are then placed at the bottom of each well of a round-bottomed 96 well microtiter plate, and 100 ul of 0.5 M NaOH is placed in each well along with a steel pin/pestle (3/32"x1/4,") although exact dimensions can vary according to tissue type or other factor). Also, multiple microfuge tubes can be used for sample collection, and processed with the mill when placed in a standard lab tray adapted to hold them. Other pin sizes have been tested, but this pestle size gives the best results for the tissue being extracted. Other sizes may work better according to other tissue types.

The power is supplied through the device herein disclosed. We have found that very short pulses as shown in the attached diagrams appear to work best for the maceration of the tissue and that a grinding time range from 15 to 45 seconds is sufficient to release enough DNA for analysis using DNA amplification protocols (i.e. PCR, RT-PCR). Other intracellular compounds are also generally available for retrieval after this time range, though it can vary by tissue type. Upon retrieval DNA can prepared for amplification through the following steps. Amplification is initiated by the following steps: a small portion of the extract (10–40 microliters) of the extract is transferred to a container such as a microfuge tube or microtiter plate well holding 200 ul of dilute buffer. The buffer that we have devised consists of 0.02 M Tris at pH 7.0 containing 0.001M EDTA for better preservation of the DNA. The DNA isolated is of sufficient quality so as to be useful for amplification procedures such as PCR. Dependent upon the tissue or cell type anti-endonucleases (i.e. anti-DNAses or RNAses) should be incorporated in minute quantities to preserve the integrity of the target intracellular compound.

Literature Referred to and Herein Incorporated

Gu, W. K., et al., *Large-scale, cost-effective screening of PCR products in marker-assisted selection applications*, Theor. Applied Genet. 91:465–470 (1995).

Saiki, R. K., et al., *Primer-directed enzymatic amplification of DNA with a thermostable DNA polymerase*, Science 239:487–491 (1988).

Wang, H., et al., *A simple method of preparing plant samples for PCR*. Nucleic Acids Res., 21:4153–4154 (1993).

Foster, A., *Cell disruption: Breaking up is hard to do*, Biotech. Vol. 10:1539–41 (1992).

What is claimed is:

1. An apparatus for simultaneous maceration of a plurality of samples, said samples containing a target molecule, comprising:
    a) a plurality of non-magnetically active containers, each adapted to hold one of said plurality of samples;
    b) a plurality of magnetically active micropestles each located in one of said non-magnetically active containers; and
    c) electromagnetic means for creating a varying electromagnetic field exerting a force upon each micropestle of said plurality of magnetically active micropestles.

2. The apparatus of claim 1 wherein said non-magnetically active containers are selected from the group consisting of:
    a) a plurality of individual plastic microfuge tubes; and
    b) a microplate with a plurality of wells arranged in a matrix.

3. The apparatus of claim 1, wherein the dimensions of said micropestles are optimized for an organic material from which said target molecule is being extracted.

4. The apparatus of claim 1, wherein said samples are organic.

5. The apparatus of claim 1, in which each of said samples is placed in a buffering solution within one of said plurality of non-magnetically active containers.

6. The apparatus of claim 5 wherein said buffering solution is alkaline.

7. The apparatus of claim 1 wherein said micropestle comprises a material selected from the group consisting of:

a) a ferromagnetic material;
b) a ferroelectric material;
c) stainless steel; and
d) a ferromagnetic ceramic.

8. The apparatus of claim 1 such that the maceration of said sample approximates the manual method of mortar-and-pestle preparation.

9. The apparatus of claim 1 wherein said electromagnetic means for creating a varying electromagnetic field comprises:
a) an upper coil assembly; and
b) a lower coil assembly.

10. The apparatus of claim 9 wherein both said upper coil assembly and said lower coil assembly comprises:
a) a plurality of cores located in proximity to said micropestles; and
b) a plurality of coils located in proximity to said plurality of said cores.

11. The apparatus of claim 10, wherein each said plurality of cores comprises:
a) peripheral driver cores; and
c) central driver cores having a length great than said peripheral driver cores; and
d) a second set of coils positioned over said central driver cores,
whereby a substantially uniform magnetic field strength is maintained across both said upper coil assembly and said lower coil assembly.

12. The apparatus of claim 11 wherein the power source for said varied electromagnetic field is a low voltage alternating current.

13. The apparatus of claim 10 wherein the varied electromagnetic field is derived from a 60 cycle ½ wave (50% duty cycle) sinusoidal current.

14. The apparatus of claim 11 wherein each of said coil assemblies operates for 200 milliseconds in an alternating fashion, the overall polarity switch operating every 400 milliseconds.

15. The apparatus of claim 1 wherein said electromagnetic means is controlled through the use of an integrated microprocessor and software.

16. The apparatus of claim 7, wherein said micropestle includes a core and an outer surface, and wherein said core comprises a ferromagnetic material and said outer surface comprises a coating selected from the group consisting of:
a) a non-reactive plastic material;
b) a polytetrafluorethylene; and
c) a ferrolectric material.

17. The apparatus of claim 1 wherein the electromagnetic field is varied such that said micropestles are moved in a psuedo-random manner.

* * * * *